(12) United States Patent
Noda et al.

(10) Patent No.: US 10,429,365 B2
(45) Date of Patent: Oct. 1, 2019

(54) CHROMATOGRAM DATA PROCESSING SYSTEM

(71) Applicant: SHIMADZU CORPORATION, Kyoto-shi, Kyoto (JP)

(72) Inventors: Akira Noda, Nara (JP); Yasuhiro Mito, Kyotanabe (JP)

(73) Assignee: SHIMADZU CORPORATION, Kyoto-Shi, Kyoto (JP)

( * ) Notice: Subject to any disclaimer, the term of this patent is extended or adjusted under 35 U.S.C. 154(b) by 72 days.

(21) Appl. No.: 15/022,626

(22) PCT Filed: Oct. 16, 2013

(86) PCT No.: PCT/JP2013/078028
§ 371 (c)(1),
(2) Date: Mar. 17, 2016

(87) PCT Pub. No.: WO2015/056311
PCT Pub. Date: Apr. 23, 2015

(65) Prior Publication Data
US 2016/0231297 A1    Aug. 11, 2016

(51) Int. Cl.
*G01N 30/86* (2006.01)
*G01N 30/74* (2006.01)

(52) U.S. Cl.
CPC ......... *G01N 30/8689* (2013.01); *G01N 30/74* (2013.01); *G01N 30/8644* (2013.01); *G01N 30/8693* (2013.01)

(58) Field of Classification Search
CPC ........... G01N 30/8689; G01N 30/8644; G01N 30/8693; G01N 30/74
See application file for complete search history.

(56) References Cited

U.S. PATENT DOCUMENTS

| 4,802,102 A | * | 1/1989 | Lacey ............... G01N 30/8624 |
| | | | 702/32 |
| 5,596,135 A | | 1/1997 | Mito et al. |
| 2004/0014146 A1 | * | 1/2004 | Wang ............... G01N 30/8689 |
| | | | 435/7.1 |

FOREIGN PATENT DOCUMENTS

CN   101256176 A  *  9/2008  ......... G01N 30/8689
JP   7-218491 A      8/1995
(Continued)

OTHER PUBLICATIONS

Written Opinion for PCT/JP2013/078028 dated Dec. 24, 2013. [PCT/ISA/237].
(Continued)

*Primary Examiner* — Michele Fan
(74) *Attorney, Agent, or Firm* — Sughrue Mion, PLLC

(57) ABSTRACT

For vector A which expresses an absorption spectrum of a target component, vector F orthogonal to vector A is designated as a filter for extracting an impurity superposed on the target component on a chromatogram. For vector I which expresses a measured spectrum obtained by a chromatographic analysis performed on a sample, the inner product of vectors I and F is defined as an index value u of the amount of impurity. If an impurity is present, a peak-like waveform appears on a graph which shows a temporal change in the index value u for the measured spectrum obtained at each point in time of the measurement. By detecting this waveform, the presence or absence of the impurity can be correctly determined. The direction of vector F may be determined so that, when vector B which expresses a spectrum of the impurity is decomposed into vector Ba parallel to vector A and vector Bo orthogonal to vector A, vector F becomes nearly parallel to vector Bo (i.e. the cosine similarity index is maximized).

12 Claims, 7 Drawing Sheets

I: VECTOR WHICH EXPRESSES PROCESS-TARGET SPECTRUM
A: VECTOR WHICH EXPRESSES SPECTRUM OF TARGET COMPONENT
B: VECTOR WHICH EXPRESSES IMPURITY SPECTRUM

(56) References Cited

FOREIGN PATENT DOCUMENTS

JP        2002-286704 A     10/2002
WO     2013/035639 A1     3/2013

OTHER PUBLICATIONS

International Search Report of PCT/JP2013/078028 dated Dec. 24, 2013.

Communication dated Jan. 21, 2019 issued by the Intellectual Property Office of India in counterpart application No. 201647009421.

* cited by examiner

WHEN SPECTRUM WHICH CONTAINS IMPURITY IS SET AS VECTOR A

WHEN SPECTRUM WHICH CONTAINS NO IMPURITY IS SET AS VECTOR A

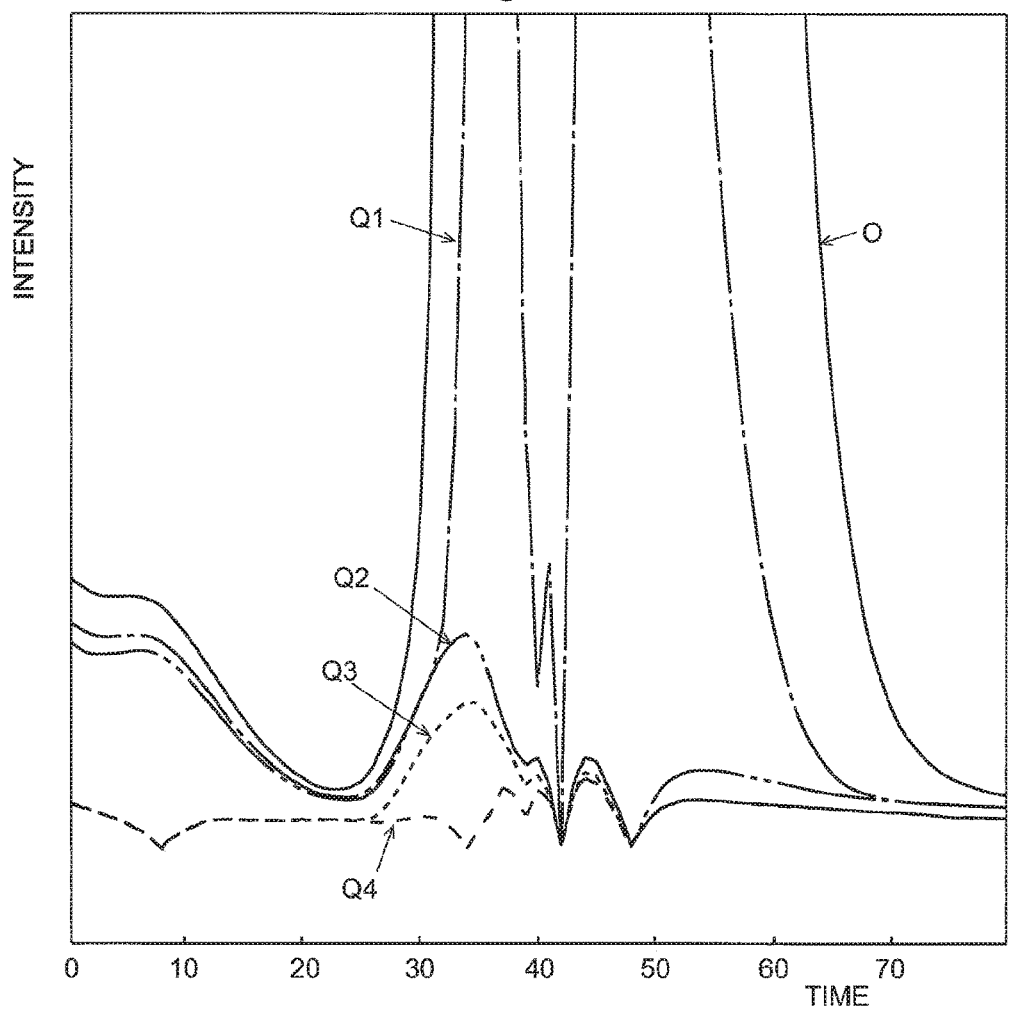
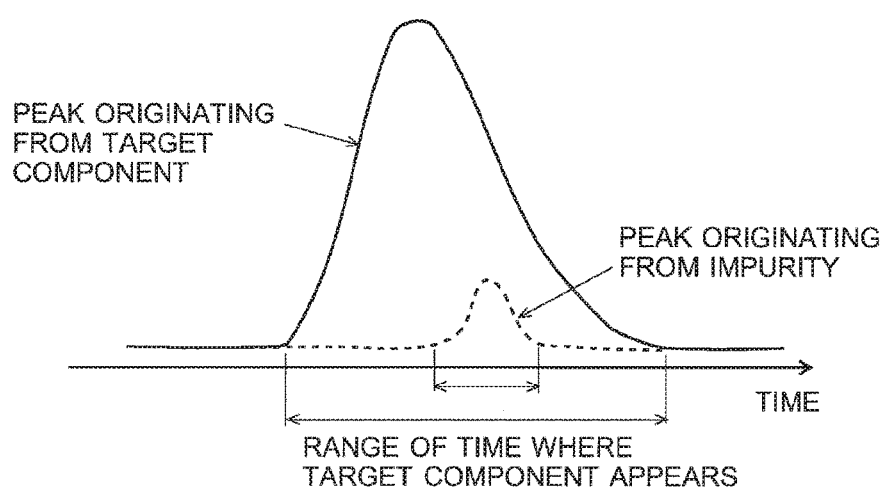

CHROMATOGRAM

A CASE WHERE IMPURITY IS DETECTABLE

A CASE WHERE IMPURITY IS DIFFICULT TO DETECT

A CASE WHERE IMPURITY IS DIFFICULT TO DETECT

CHROMATOGRAM DATA PROCESSING SYSTEM

CROSS REFERENCE TO RELATED APPLICATIONS

This is a National Stage of International Application No. PCT/JP2013/078028 filed Oct. 16, 2013, the contents of which are incorporated herein by reference in its entirety.

TECHNICAL FIELD

The present invention relates to a chromatogram data processing system for processing three-dimensional chromatogram data collected by repeatedly performing a spectroscopic analysis or mass-spectrometric analysis of a sample containing a component separated by a chromatograph (e.g. liquid chromatograph) or a sample introduced by a flow injection method. More specifically, it relates to a data processing system for determining the presence or absence of an impurity or other similar components superposed on a peak originating from a target component appearing on a chromatogram.

BACKGROUND ART

With a liquid chromatograph in which a multichannel detector, such as a photo diode array (PDA) detector, is used as the detector, three-dimensional chromatogram data having the three dimensions of time, wavelength and absorbance can be obtained by repeatedly acquiring an absorption spectrum for an eluate from the exit port of a column, with the point in time of the injection of the sample into the mobile phase as the base point. Similarly, with a liquid chromatograph (LC) or gas chromatograph (GC) in which a mass spectrometer is used as the detector, three-dimensional chromatogram data having the three dimensions of time, mass-to-charge ratio and signal intensity can be obtained by repeatedly performing a scan measurement over a predetermined mass-to-charge-ratio range in the mass spectrometer. The following description deals with the case of a liquid chromatograph using a PDA detector, although the case is the same with a chromatograph using a mass spectrometer as the detector.

FIG. 8A is a model diagram showing three-dimensional chromatogram data obtained with the aforementioned liquid chromatograph. By extracting absorbance data at a specific wavelength (e.g. $\lambda 0$) from the three-dimensional chromatogram data a wavelength chromatogram showing the relationship between the measurement (i.e. retention time) and the absorbance at that specific wavelength as shown in FIG. 8B can be created. Furthermore, by extracting data which show the absorbance at a specific point in time (measurement time) from the three-dimensional chromatogram data, an absorption spectrum showing the relationship between the wavelength and the absorbance at that point in time can be created.

In such a liquid chromatograph, a quantitative analysis of a known target component is normally performed as follows: A wavelength chromatogram at an absorption wavelength corresponding to that target component is created. On this wavelength chromatogram, the beginning point Ts and ending point Te of a peak originating from the target component are located. The area value of that peak is calculated, and the quantitative value is computed by comparing that area value with a previously obtained calibration curve.

There is no problem with such a quantitative determination of a target component if the peak which has appeared on the extracted wavelength chromatogram originates from only that target component. However, a peak is not always composed of only a single component (target component); it is often the case that a signal originating from an impurity unintended by the analysis operator (or more broadly, any component other than the intended one) is superposed on the peak. If the analysis operator performs the quantitative calculation without noticing such a situation, the result of the quantitative determination will be inaccurate. Accordingly, an impurity determination process (or peak purity determination process) for examining whether a peak located on a chromatogram has originated from only the target component or additionally contains an impurity is often performed in advance of the quantitative calculation.

To date, various methods have been proposed and practically used as the impurity determination process for a peak on a chromatogram. However, the actual situation is such that none of the conventional methods is a decisive solution since each method has both advantages and disadvantages.

For example, in the impurity determination method described in Patent Literature 1, the absorption spectrum obtained at each point in time of the measurement is differentiated with respect to wavelength at a maximum (or minimum) absorption wavelength of the target component to calculate a wavelength differential coefficient, and a differential chromatogram showing the temporal change of the wavelength differential coefficient is created. Whether or not a peak originating from the target component on the wavelength chromatogram contains an impurity is judged by determining whether or not a peak waveform similar to the one which appears on a normal chromatogram is observed on the differential chromatogram. This method is excellent in that whether or not an impurity exists can be determined with a high level of reliability by comparatively simple computations. However, in principle, there is the case where an impurity cannot be detected, as will be hereinafter described.

FIGS. 9A-9C show examples of the relationship between the absorption spectrum originating from a target component (solid line) and the absorption spectrum originating from an impurity (broken line).

In the previously described conventional impurity determination method, as shown in FIG. 9A, the wavelength differential coefficient of the absorption spectrum curve of the impurity at wavelength $\lambda 0$ where the extreme point of the absorption spectrum originating from the target component is located (i.e. the wavelength at which the wavelength differential coefficient is zero) is used for the impurity determination. As shown in FIG. 9A, if the wavelength at which the absorption spectrum of the impurity is maximized does not coincide with wavelength and therefore the spectrum curve has a certain slope at wavelength $\lambda 0$, the impurity can be detected. However, as shown in FIG. 9B, if both the extreme point of the absorption spectrum originating from the target component and that of the absorption spectrum originating from the impurity appear at the same wavelength, the wavelength differential coefficient of the absorption spectrum curve of the impurity becomes almost zero, so that the impurity cannot be detected.

Furthermore, as shown in FIG. 9C, if the curve of the absorption spectrum originating from the impurity has a low slope (which can be horizontal in an extreme case) in the vicinity of the extreme point of the absorption spectrum originating from the target component, the impurity-originated peak which appears when the differential chromatogram is created may become extremely low and obscured by noise components, so that it will be ultimately impossible to detect the impurity.

In the case where the sample is introduced by a flow injection analysis (FIA) method without using the column and detected with a PDA detector or similar device, the obtained data will also be three-dimensional data having the three dimensions of time, wavelength and absorbance. Such data are practically equivalent to the three-dimensional chromatogram data collected with a liquid chromatograph. Therefore, three-dimensional data collected by the FIA method should also be included with the "three-dimensional chromatogram data" in the present description.

CITATION LIST

Patent Literature

Patent Literature 1: WO 2013/035639 A

SUMMARY OF INVENTION

Technical Problem

The present invention has been developed to solve the previously described problem. Its objective is to provide a chromatogram data processing system capable of correctly and stably determining the presence or absence of the superposition of an impurity on a target peak on a chromatogram even in such a case where the presence or absence of the superposition of the impurity cannot be easily and correctly determined by the previously described conventional impurity determination method.

Solution to Problem

The present invention developed for solving the previously described problem is a chromatogram data processing system for processing three-dimensional chromatogram data having time, signal intensity and another third dimension collected for a sample to be analyzed, the system including:

a) a filter creator for calculating one auxiliary vector orthogonal to a principal vector which is a multidimensional vector expressing a spectrum which shows or can be regarded as the relationship between the third dimension and the signal intensity for the target component to be observed, and for designating the auxiliary vector as a filter for impurity extraction; and b) an impurity presence information acquirer for calculating the inner product of a process-target multidimensional vector and the auxiliary vector designated as the filter, the process-target multidimensional vector expressing a process-target spectrum obtained or derived from the three-dimensional chromatogram data obtained for the sample to be analyzed, and for determining the presence or absence of an impurity other than the target component in the process-target spectrum based on a result of the calculation.

For example, the "third dimension" in the present context is the wavelength or mass-to-charge ratio, while the "three-dimensional chromatogram data" are a net of data obtained by repeatedly acquiring an absorption spectrum with a multichannel detector or similar detector, or a set of data obtained by repeatedly acquiring a mass spectrum with a mass spectrometer, for a sample containing various components temporally separated by a column of a chromatograph (LC or GC). The "three-dimensional chromatogram data" may also be a set of data obtained with a multichannel detector or mass spectrometer for a sample introduced by the HA method without being separated into components, instead of the sample which has passed through the column of a chromatograph.

In the chromatogram data processing system according to the present invention, a spectrum which shows the relationship between the third dimension and the signal intensity (e.g. an absorption spectrum or mass spectrum) is expressed by a vector and handled as the multidimensional vector. For example, consider the case of an absorption spectrum. An absorption spectrum is a set of values showing the absorbance at discrete wavelengths. Therefore, the absorption spectrum can be expressed as $(a(\lambda 1), a(\lambda 2), a(\lambda 3), \ldots, a(\lambda n))$, and a multidimensional vector with $a(\lambda m)$ as its elements can be defined, where $a(\lambda m)$ represents absorbance at wavelength $\lambda m$ ($m=1 \ldots n$).

With I denoting the process-target multidimensional vector which expresses the process-target spectrum at a specific point in time of the measurement, A denoting the multidimensional vector which expresses the spectrum of the target component, and B denoting the multidimensional vector which expresses the spectrum of the impurity, the process-target multidimensional vector can be expressed as a vector operation by the following equation (1):

$$I=A+B \qquad (1)$$

Suppose that vector B expressing the spectrum of the impurity is decomposed into vector Ba which is parallel to vector A expressing the spectrum of the target comp a d vector Bo which is orthogonal to vector A. Suppose there is also another multidimensional vector F orthogonal to vector A. Since any two mutually orthogonal vectors have an inner product of zero, the inner product of the vectors F and Ba equals zero. Accordingly, the if product of the process-target multidimensional vector I and vector F equals that of the vectors Bo and F. That is to say, the following equation (2) holds true:

$$I \cdot F = Bo \cdot F \qquad (2)$$

Since the length of vector Bo is proportional to that of vector B expressing the spectrum of the impurity, the right-hand side of equation (2), Bo·F, is also proportional to the length of vector B. Accordingly, the inner product of the vectors on the left-hand side of equation (2), I·F, is also proportional to the length of vector B expressing the spectrum of the impurity. This means that the inner product of the vectors I·F can be used as an index value u which represents the amount of impurity. Accordingly, in the chromatogram data processing system according to the present invention, the filter creator calculates an auxiliary vector F orthogonal to the principal vector A expressing the spectrum of the target component, and designates it as the filter for impurity extraction. The impurity presence information acquirer calculates the inner product of vector I expressing the process-target spectrum obtained or derived from the three-dimensional chromatogram data and vector F designated as the filter, and determines whether or not an impurity exists based on the result of the calculation.

As one typical mode, the impurity presence information acquirer may be configured so that, for each of the process-target spectra obtained at the respective points in time of the measurement with the passage of time, it calculates the inner product of vector I expressing the spectrum and vector F designated as the filter, observes the change in the value of the inner product along the time series, and determines that an impurity other than the target component exists when, for example, a waveform similar to a chromatogram peak has appeared.

In the chromatogram data processing system according to the present invention, the filter creator calculates, as the filter for impurity extraction, the auxiliary vector orthogonal to the multidimensional principal vector. There are many vectors orthogonal to a given vector in a multidimensional vector space. Accordingly, the filter creator should preferably determine the direction of the auxiliary vector F so that the cosine similarity index between vector Bo originating from the spectrum of the impurity and the auxiliary vector F designated as the filter for vector Bo will be maximized, i.e. as close to "1" as possible. By this operation, the SN ratio of the index value u of the amount of impurity expressed by equation (2) becomes maximized or close to that level, which improves the correctness in the determination on the presence or absence of non-target components.

To calculate the cosine similarity index, vector Bo needs to be calculated. This can be analytically determined as follows:

$$Bo = I - \alpha A$$

$$\alpha = (I \cdot A)/(A \cdot A) \quad (3)$$

When the inner product of the vectors I and F is calculated in the previously described manner for each of the process-target spectra obtained at the respective points in time of the measurement, the vector F obtained at each point in time of the measurement may be used or alternatively, one or more representative vectors F may be used.

For example, as one embodiment, the filter creator may determine an average vector of a plurality of vectors which are the filters for impurity extraction created at the respective points in time of the measurement, and the impurity presence information acquirer may use the average vector in calculating the inner product for each vector which expresses the process-target spectrum obtained at each point in time of the measurement.

By this configuration, a vector which is robust against noise can be used as the filter for impurity extraction, so that the presence or absence of an impurity can be correctly determined even when a noise component is superposed on the data.

An another embodiment, the filter creator may select a vector having the largest norm from among a plurality of vectors which are the filters for impurity extraction created at the respective points in time of the measurement, and the impurity presence information acquirer may use the selected vector in calculating the inner product for each vector which expresses the process-target spectrum at each point in time of the measurement.

If there are a plurality of impurities, the auxiliary vector which is the filter for impurity extraction at each point n time of the measurement will be a mixture of the signals originating from a plurality of spectra. In such a case, a vector obtained by a simple averaging operation may not correctly show the presence of the impurities. Accordingly, as still another embodiment, the filter creator may compute a cluster mean for a plurality of vectors which are the filters for impurity extraction created at the respective points in time of the measurement, and the impurity presence information acquirer may use the vector of the cluster mean in calculating the inner product for each vector which expresses the process-target spectrum at each point in time of the measurement.

For obtaining the cluster mean, the k-mean clustering, me shift or similar methods can be used. It is also possible to use a smoothing filter in which time-series fluctuations are taken into account, such as the moving average, bilateral filter, Kalman filter or particle filter.

As still another embodiment of the chromatogram data processing system according to the present invention, the filter creator may designate, as the filter for impurity extraction, a vector obtained by multiplying the vector expressing the spectrum of the target component by a predetermined constant and subtracting the multiplied vector from the vector expressing the process-target spectrum. In other words, from equation (3), the vector which expresses the filter in this case is Bo itself.

In this case, the impurity presence information acquirer may calculate the secondary norm of the vector created as the filter for impurity extraction by the filter creator and use the secondary norm in place of the inner product to determine the presence or absence of an impurity in the process-target spectrum. This enables an easy and fast calculation of the index value of the amount of impurity. This is particularly advantageous in the previously described case of calculating the index value of the amount of impurity for each of the process-target spectra obtained at the respective points in time of the measurement with the passage of time.

The chromatogram data processing system according to the present invention may preferably be configured so that, if it is determined by the impurity presence information acquirer that an impurity is present, a spectrum expressed by the vector created as the filter for impurity extraction by the filter creator, e.g. the vector expressed by is designated as a residual spectrum, and the processes performed by the filter creator and the impurity presence information acquirer are repeated using the residual spectrum as the process-target spectrum.

By this configuration, when there are a plurality of impurities mixed in the sample, even if all of them cannot be detected by a single processing operation by the filter creator and the impurity presence information acquirer, the remaining impurities can be detected in a stepwise manner while the process is repeated a plurality of times.

In the chromatogram data processing system according to the present invention, it is basically preferable to use, as vector A, a vector which truly expresses the spectrum of the target component. However, in general, the exact spectrum of the target component is often unknown. Accordingly, it is common to use a spectrum which can be regarded as the target component, and not the true spectrum of the target component.

As one preferable mode, the fitter creator may regard, as the spectrum of the target component, a spectrum based on data obtained within a period of time which is estimated to include the target component free of impurities among the three-dimensional chromatogram data obtained for the sample to be analyzed, and create a vector expressing this spectrum as the principal vector, i.e. vector A. The position where a target component free of impurities is estimated to be present may be located by an analysis operator, although the position may automatically be determined by automatically examining the shape of the chromatogram peak.

As another mode, the filter creator may designate, as the principal vector (i.e. vector A), a spectrum having the largest norm when expressed in the form of a vector among the spectra based on the three-dimensional chromatogram data obtained for the sample to be analyzed.

This makes it possible to perform the impurity determination process without previously determining the spectrum of the target spectrum.

Basically, vector A should be a vector which expresses an impurity-free spectrum. However, in some cases, the spectrum contains an impurity, and the consequently created filter for impurity extraction also contains the impurity. In such a case, plotting the inner product of the vectors I F in time-series order results in a peak appearing before and after the point in time of the measurement at which the spectrum selected as vector A is obtained. This is due to the fact that the influence of the additional deduction of the impurity from the spectrum selected as vector A appears before and after the point in time of the measurement. This fact can also be used to determine whether or not an impurity is present at a certain point in time of the measurement or within a specific range of time.

Thus, the chromatogram data processing system according to the present invention may be configured so that:

the filter creator designates, as the spectrum of the target component, a spectrum based on data obtained within a specific period of time among the three-dimensional chromatogram data obtained for the sample to be analyzed, multiplies a vector expressing the spectrum of the target component by a predetermined constant, and designates, as the filter for impurity extraction, a vector obtained by subtracting the multiplied vector from the vector expressing the process-target spectrum; and the impurity presence information acquirer designates, as a residual spectrum, a spectrum expressed by the vector created as the filter for impurity extraction by the filter creator for each of the spectra obtained within a predetermined range of time including the specific period of time, and determines whether or not an impurity is present within the specific period of time by determining whether or not a peak appears before and after the specific period of time on a chromatogram created for the predetermined period of time based on the residual spectrum.

Advantageous Effects of the Invention

The chromatogram data processing system according to the present invention can correctly and stably determine whether or not an impurity is contained in a target peak on a chromatogram created based on three-dimensional chromatogram data collected with a chromatograph in which a multichannel detector (e.g. PDA detector) or mass spectrometer is used as the detector. In particular, the presence or absence of a superposition of an impurity can be correctly and stably determined even in the case where it is difficult to appropriately determine the presence or absence of the superposition of the impurity by the previously described impurity determination method which uses the differential chromatogram.

BRIEF DESCRIPTION OF DRAWINGS

FIG. 6 shows one example of the change in the waveform showing the temporal change in the index value of the amount of impurity in the case where the impurity separation process is repeated a plurality of times in the liquid chromatograph of the present embodiment.

FIG. 7 illustrates the impurity determination process in the liquid chromatograph of the present embodiment.

DESCRIPTION OF EMBODIMENTS

One embodiment of the chromatogram data processing system according to the present invention is described with reference to the attached drawings.

As described earlier, the present chromatogram data processing system has the function of determining whether or not an impurity is contained in a peak on a chromatogram (see FIG. 8B) created based on three-dimensional chromatogram data (see FIG. 8A) which have been collected, for example, by using a liquid chromatograph having a PDA detector. Initially, the principle of the impurity determination process in the chromatogram data processing system according to the present invention is described.

[Principle of Impurity Determination Process]

In the present impurity determination process, both a set of process-target spectra sequentially obtained with the passage of time (in the following description, a "spectrum" means an absorption spectrum with the horizontal axis indicating wavelength and the vertical axis indicating absorbance; however, as already noted, the description similarly holds true for a mass spectrum or other types of spectra) and a spectrum of the target component are used to create a graph with a high SN ratio which shows the temporal change in an index value of the amount of impurity other than the target component. Whether or not an impurity is contained in a peak on the chromatogram is determined by examining whether or not a chromatogram-peak-like signal exists on the graph.

Figure 8A:
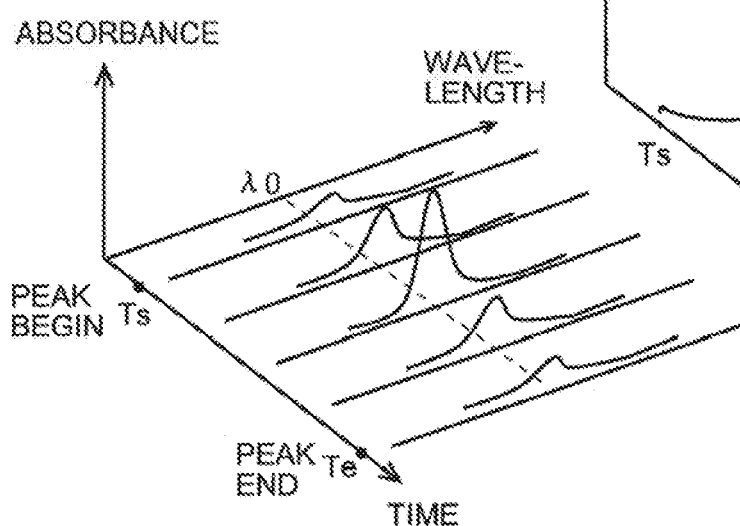
FIG. 8A is a model diagram of the three-dimensional chromatogram data obtained with a liquid chromatograph.
Figure 8B:
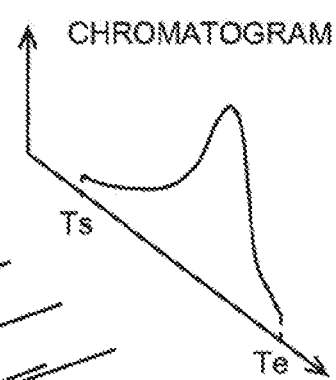
FIG. 8B is a waveform chromatogram.
Figure 9A:
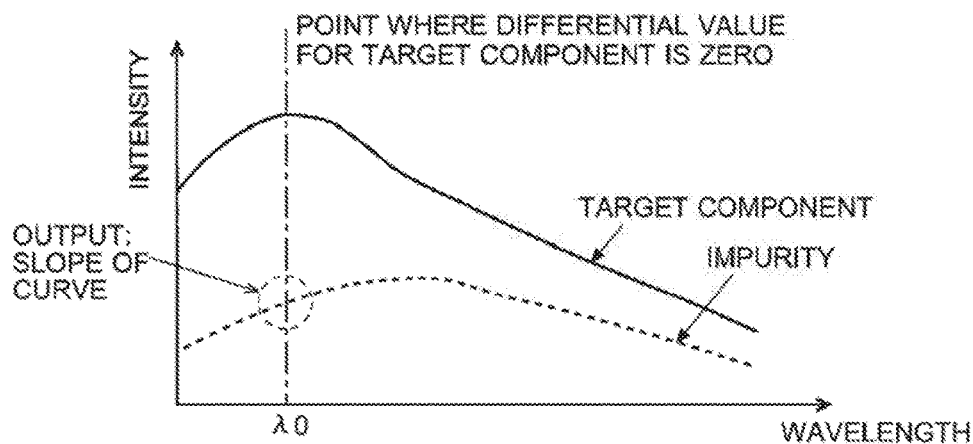
FIGS. 9A-9C show examples of the absorption spectrum for explaining a problem concerning a conventional impurity determination process which uses the differential chromatogram.
Figure 9B:
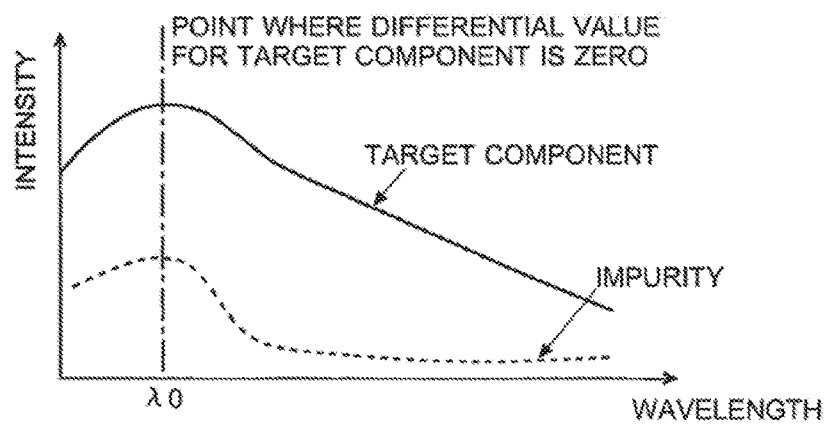
Figure 9C:
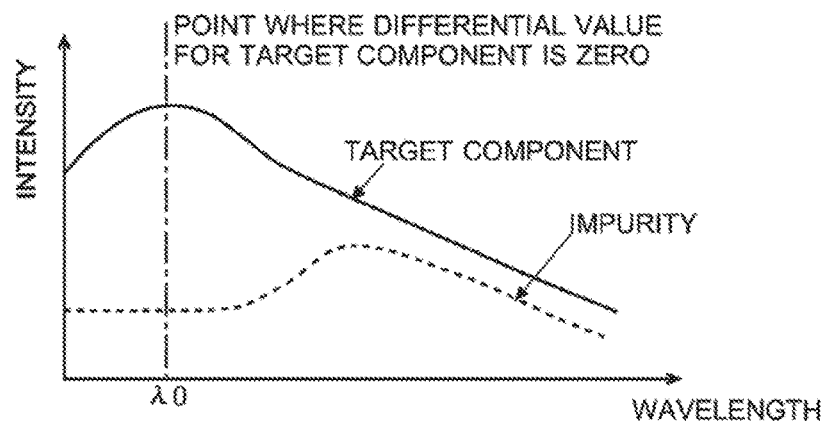

Suppose that vector I expresses a process-target spectrum at a certain point in time of the measurement, and vector A expresses a spectrum of the target component (or a spectrum which can be regarded as a spectrum of the target component). Typically, the process-target spectrum is a spectrum which shows the absorbance at a certain point in time extracted from three-dimensional chromatogram data (such as shown in FIG. 8A). However, as will be described later, when the impurity separation process is repeated, the spectrum which has undergone the separation process is handled as the process-target spectrum.

Figure 3:
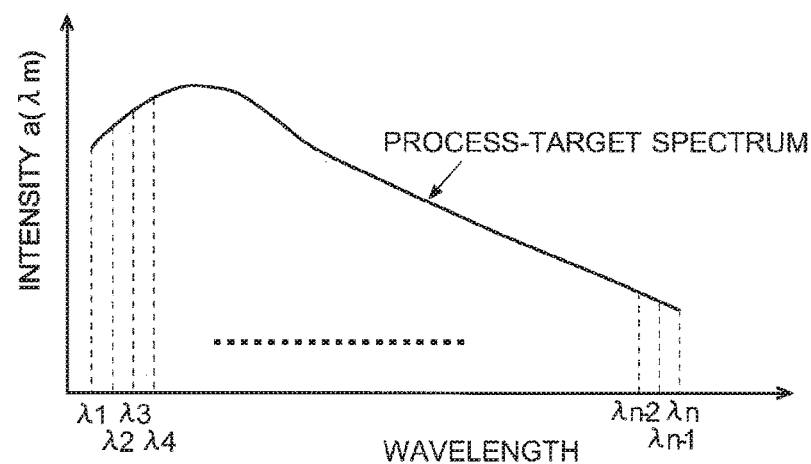
FIG. 3 shows one example of the absorption spectrum obtained at a certain point in time of the measurement.

In the present description, the spectrum as shown in FIG. 3 is regarded as a set of absorbance data at discrete wavelengths within a predetermined wavelength range. The absorption spectrum is expressed by $(a(\lambda 1), a(\lambda 2), a(\lambda 3), \ldots, a(\lambda n))$, where $a(\lambda m)$ represents absorbance at wavelength λm (m=1 ... n). A spectrum in this notation can be expressed as a vector in an n-dimensional space. In other words, this spectrum is a multidimensional vector with a(λ1), a(λ2), a(λ3), ... as its elements. Similarly, the spectrum of the impurity is expressed by vector B. As already noted, vector I which expresses the process-target spectrum can be expressed by equation (1):

$$I=A+B \quad (1)$$

Figure 4:
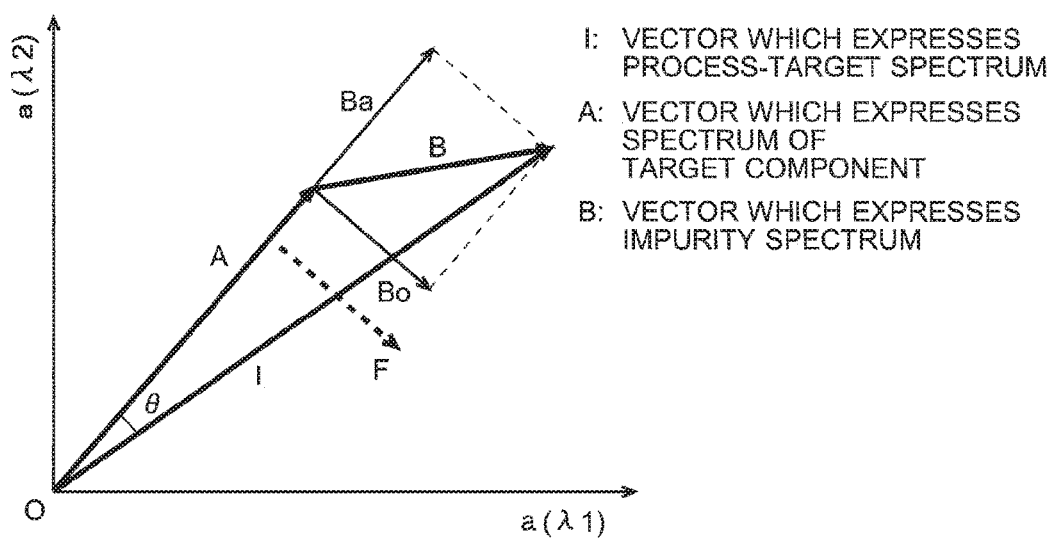
FIG. 4 illustrates the principle of the impurity determination process in the present invention.

FIG. 4 shows the two-dimensional vector space, which is a simple version of the n-dimensional vector space. The relationship of I, A and B given by equation (1) is as shown in FIG. 4.

Suppose that vector B expressing the spectrum of the impurity is decomposed into vector Ba which is parallel to vector A expressing the spectrum of the target component and vector Bo which is orthogonal to vector A. Suppose also there is another multidimensional vector F orthogonal to vector A. Since vector Ba is parallel to vector A while vector F is orthogonal to vector A, vectors F and Ba are orthogonal to each other. Since any two mutually orthogonal vectors have an inner product of zero, the inner product of vectors F and Ba is equal zero. Accordingly, the inner product of the multidimensional vector I to be processed and vector F is equal that of the vectors Bo and F. That is to say, the already mentioned equation (2) holds true:

$$I \cdot F = Bo \cdot F \quad (2)$$

Since the length of vector Bo is naturally proportional to that of vector B expressing the spectrum of the impurity, the right-hand side of equation (2), Bo·F, is proportional to the length of vector B, i.e. the amount of impurity. Accordingly, the inner product of the vectors on the left-hand side of equation (2), I·F, can be used as an index value u which represents the amount of impurity. In this operation, vector F is used for extracting impurity components from vector I representing the process-target spectrum. Therefore, vector F is designated as the filter for impurity extraction. For example, in the case of determining whether or not an impurity is superposed on a peak originating from a target component which appears on an appropriate type of chromatogram such as a waveform chromatogram), it is possible to conclude that an impurity is present if a chromatogram-peak-like waveform has appeared on a graph which shows the temporal change in the index value u (=inner product I·F) over the range from the beginning point to the ending point of the peak.

In an n-dimensional vector space having an extremely large value of n, there are virtually infinite number of vectors orthogonal to vector A expressing the spectrum of the target component. In the case of using the inner product I·F as the index value u of the amount: of impurity, it is preferable to determine the direction of vector F expressing the filter for impurity extraction as follows:

Consider the case where white noise is superposed on vector I expressing the process-target spectrum. The signal component which is included in the inner product due to this white noise is independent of the deflection angle of vector F and is proportional to the length of this vector. The closer to the angle the angle made by vector Bo originating from the impurity and vector F becomes, the greater influence the signal component included in the inner product due to the white noise has on the extraction of the impurity component. This conversely means that vectors F and Bo should be as parallel to each other as possible in order to increase the SN ratio of the signal originating from the impurity in the inner product I·F. In other words, it is preferable to determine the direction of vector F relative to Bo so that their cosine similarity index becomes the maximum or as close to the maximum as possible. To this end, it is naturally necessary to determine vector Bo, which can be analytically calculated by the already mentioned equation (3):

$$Bo=I-\alpha A$$

$$\alpha=(I \cdot A)/(A \cdot A) \quad (3)$$

In some cases, a variation occurs in the spectrum of the impurity due to a pH change of the sample liquid (in the case of a liquid chromatograph), non-linearity of the detector or other factors, which may cause a variation in the index value u of the amount of impurity expressed as the inner product I·F and the consequent occurrence of a peak-like false waveform on the graph of the index value u. However, the variation of the spectrum due to the aforementioned factors shows a certain definite pattern of change, so that the change in the waveform which occurs in the index value u can be discriminated from the change in the waveform due to the mixture of an impurity. Accordingly, when displaying the result of the impurity determination process, it is preferable to show both the index value u of the amount of impurity expressed by the inner product of vectors I·F (or a graph showing the temporal change in the index value u d the spectrum expressed as vector Bo so that an analysis operator can visually examine the result and determine whether or not an impurity is truly superposed and what characteristics the spectrum of the detected impurity has.

The spectrum expressed by the thereby displayed vector Bo is not the intact spectrum of the impurity; it is the spectrum from which the vector component Ba parallel to vector A has been removed. Accordingly, attention must be paid to the fact that, when a spectrum of a pure substance recorded in a database is additionally displayed or a database search is performed in order to identify an impurity based on the spectrum concerned or compare this spectrum with another one, it is necessary to previously remove the component parallel to vector A from the spectrum of the pure substance.

In the case where the graph showing the temporal change in the index value u expressed by the inner product over a certain period of time is created in the previously described manner, the process-target spectrum exists at each point in time of the measurement within that period of time, and the inner product is calculated for each of those spectra. The vectors I and F with the time element taken into account are hereinafter denoted by I(t) and F(t), respectively, to show that these vectors I and F include time as one element. Vector I(t) which expresses the process-target spectrum exists at every point in time of the measurement, whereas vector F(t) which expresses the filter is not always necessary for each point in time of the measurement. There are the following two major forms of F(t) which can be used in calculating the inner product I(t)·F(t) at each point in time of the measurement:

(1) Vector F(t) calculated at each point in time of the measurement is directly used; i.e. the inner product I(t)·F(t) is calculated by multiplying vector I(t) which expresses the process-target spectrum obtained at each point in time of the measurement by F(t).

(2) Instead of directly using vector F(t) calculated at each point in time of the measurement, a vector F(t)' for the calculation of the inner product is computed from the values of F(t) obtained at the respective points in time of the measurement. For example, an average of the values of vector F(t) obtained at a plurality of points in time of the measurement within a predetermined period of time is calculated as vector F, and vector I(t) which expresses the process-target spectrum obtained at each point in time of the measurement is multiplied by vector F to calculate the inner product I(t)·F. By this method, vector F which expresses an average filter having a high level of robustness against noise can be obtained.

If a plurality of impurities are contained, vector F(t) at each point in time of the measurement will be a complex mixture of signals originating from the spectra of the plurality of impurities, since those impurities do not appear at the same timing. In such a case, the previously described simple averaging of the vectors does not provide a vector F which expresses a proper filter. Therefore, it is preferable to use the so-called "mean clustering" or similar method instead of the simple averaging. For obtaining the cluster mean, commonly known techniques can be used, such as the k-mean clustering or mean shift methods, as well as various kinds of smoothing filters in which time-series fluctuations are taken into account, such as the moving average, bilateral filter, Kalman filter or particle filter (sequential Monte Carlo method).

[Alternative to Spectrum of Target Component]

In the previous description, vector A which expresses the spectrum of the target component is used to calculate the index value u of the amount of impurity. However, in many cases, the exact spectrum of the target component is unknown. Furthermore, acquiring this spectrum requires a considerable amount of time and labor. Accordingly, in practice, it is preferable to create a pseudo spectrum of the target component from the signals obtained by the analysis on the sample (i.e. from the spectra obtained at the respective points in time of the measurement). One example is as follows:

In general, the concentration of an impurity is lower than that of the target component. Therefore, as shown in FIG. 7, the peak width of an impurity on a chromatogram is narrower than that of the target component. From this fact, it s highly likely that the spectra obtained at the respective points in time of the measurement by the analysis include both a spectrum which is composed of the spectrum of the target component with the spectrum of an impurity mixed, and a spectrum which is purely composed of the target component. Accordingly, for example, it is possible to extract, from the chromatogram data obtained by the analysis, a piece of data included within a specific range of time which is most likely to include the target component with no mixture of impurities, and to regard a spectrum obtained from the extracted data as the spectrum of the target component. It is also possible to smooth the data obtained by the analysis along the temporal direction before extracting the data from a specific range of time, or average the data obtained by the analysis within a specific range of time, and regard the thereby obtained spectrum as the spectrum of the target component. The range of time for the extraction of the data may be specified by the analysis operator. Alternatively, it may be selected in such a manner that the period of time which includes the peak of an impurity is located by a determination process (which will be described later) and a range of time within which impurities are least likely to be present is automatically selected based on the result of the determination.

If the analysis is merely aimed at determining the presence or absence of the superposition of an impurity and it is unnecessary to accurately determine the content of the impurity, it is of no consequence that the peak which occurs in the graph showing the temporal change in the index value u of the amount of impurity is split into two the reason for this splitting will be described later). In such a case, it is possible to allow for the mixture of impurities or the fluctuation of the spectrum, and simply select, as the spectrum of the target component, the spectrum having the highest SN ratio from among the spectra obtained by the analysis, which is normally a spectrum having the largest norm when expressed in the form of a vector.

Figure 5A:
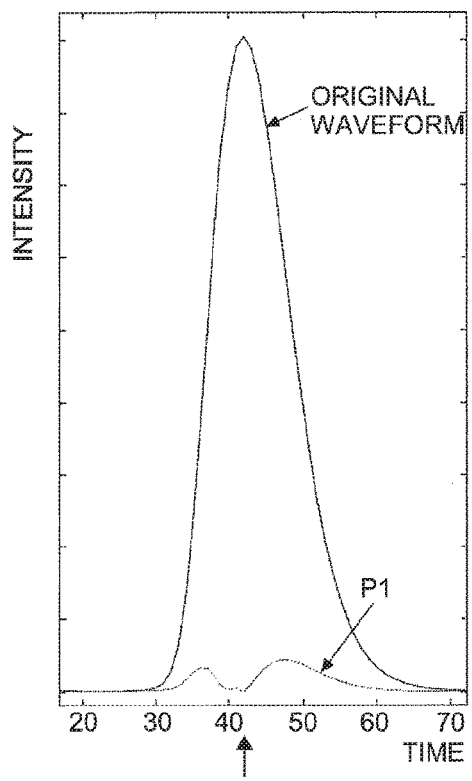
FIGS. 5A and 5B show one example of the chromatogram waveform and a waveform which shows the temporal change in an index value of the amount of impurity based on a residual spectrum in the liquid chromatograph of the present embodiment.
Figure 5B:
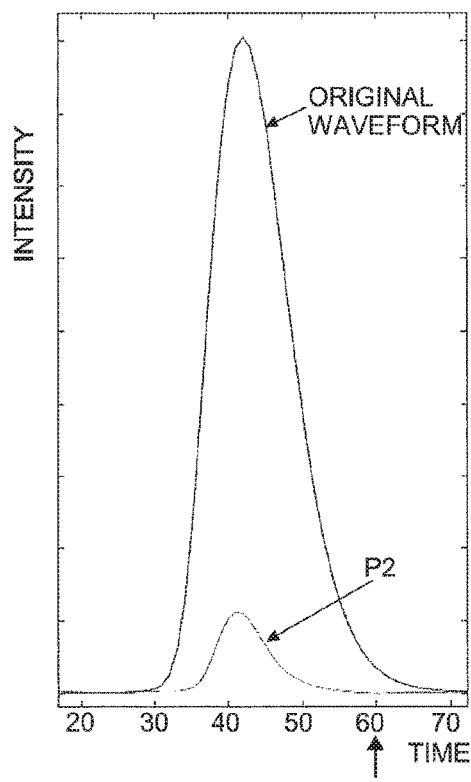

Hereinafter described with reference to FIGS. 5A and 5B is a situation which occurs in the case where the filter for impurity extraction created from a spectrum obtained at a certain point time of the measurement or a plurality of spectra obtained at the points in time of the measurement within a certain range of time is a filter created from a spectrum which contains an impurity and is not a single-component spectrum. FIGS. 5A and 5B show one example of the chromatogram waveform and a waveform which shows the temporal change in an index value of the amount of impurity based on a residual spectrum.

The index value denoted by P1 in FIG. 5A is a curve showing the inner product I(t)·F plotted against time, with the filter-expressing vector F calculated under the condition that the spectrum obtained at the measurement point in time of 42 (this spectrum contains an impurity mixed in the target component) is regarded as the spectrum of the target component. By comparison, the index value denoted by P2 in FIG. 5B is a curve showing the inner product I(t)·F plotted against time, with the filter-expressing vector F calculated under the condition that the spectrum obtained at the measurement point in time of 60 (this spectrum is purely composed of the target component with no impurity contained) is regarded as the spectrum of the target component. In FIG. 5A, two peaks are located before and after the measurement point in time at which the spectrum of the target component is selected. This is the aforementioned splitting of the peak. In this case, it is difficult to determine the amount of impurity, since the shape of the peaks on the graph showing the temporal change in the inner product I(t)·F does not correctly represent the amount of impurity. However, this situation is also useful; i.e. when two peaks are located before and after the target component on the graph of the inner product I(t)·F, it is possible to consider that a spectrum which contains an impurity has been designated as the spectrum of the target component. On the other hand, as shown FIG. 5B, when a spectrum which contains no impurity is selected as the spectrum of the target component, a peak with a Gaussian waveform appears on the graph showing the temporal change in the inner product I(t)·F. This peak can be considered to be correctly representing the amount of impurity.

[Impurity Separation Process in the Case where a Plurality of Impurities are Present]

In the example shown in FIGS. 5A and 5B, the number of impurities is one. As already noted, the number of impurities mixed in the sample is not always one; there may be a plurality of impurities. Consider the case where two impurities b and c are present in addition to the target component a, with the amount of impurity c being extremely lower than the amount of the target component a or impurity b. In the case where the average of the values of F(t) at the respective points in time of the measurement within a predetermined range of time is used as vector F which expresses the filter for impurity extraction, the average vector is approximately identical to vector F which is calculated for a spectrum expressed by vector I(t) composed of vector A which expresses the spectrum of the target component a and vector B which expresses the spectrum of the impurity b. In that case, vector F is parallel to vector Bo. In this situation, if vector B is orthogonal to vector C which expresses the spectrum of the impurity c it is absolutely impossible to detect vector C on the graph showing the temporal change in the inner product I(t)·F. Even in the case where vector F(t) which expresses the filter for impurity extraction is calculated for each point in time of the measurement, the extremely low peak originating from the impurity c is difficult to detect; for example, if the peak originating from the impurity c is superposed on the base portion of the peak originating from the impurity b or similar portion where the signal significantly fluctuates, the peak will be extremely difficult to detect. Accordingly, in such a case, i.e. when the mixture of a plurality of impurities is expected and each of them needs to be detected, it is preferable to follow the hereinafter described procedure:

As can be understood from the aforementioned equation (3), I−αA represents the amount of impurity. Therefore, the process expressed by equation (2), i.e. the process of multiplying the process-target spectrum by the filter can be considered to be an impurity separation process. The spectrum expressed by vector I−αA or I(t)−αA can be considered to be a residual spectrum which remains after the removal of the target component or one or more impurities. If the sample contains a plurality of impurities, it is preferable to perform the impurity separation process in such a manner that I(t)−αA (the vector expressing the residual spectrum) calculated in the nth process is used as vector I(t) expressing the process-target spectrum for the (n+1)th process. Such a method is hereinafter called the "multistage spectrum residue method".

FIG. 6 shows signal waveforms based on the residual spectrum obtained when the multistage spectrum residue method is performed. In this figure, "O" denotes the original chromatogram waveform, while Q1-Q4 denote |I(t)| for n=1–4, respectively. Q1 should have a small peak similar to the one observed in Q3. However, in the waveform of Q1, it is difficult to visually locate the peak observed in Q3, which should also be contained in Q1. However, such a peak of the impurity which cannot be initially located can be detected by using the previously mentioned multistage spectrum residue method.

In the multistage spectrum residue method, it is preferable to determine the presence or absence of an impurity at each stage by examining whether or not a peak is present in the difference between |I(t)| obtained in the nth process and |I(t)| obtained in the (n+1)th process ("spectrum residue difference").

For example, in FIG. 6, for the impurity which is detected as a convex portion in the left part of the curve denoted by Q2, it is difficult to determine, from Q2, whether the peak is a true peak or a noise fluctuation, since the signal of Q3 is mixed in Q2. However, in the waveform denoted by Q4 obtained by removing Q3, it is possible to recognize the presence of a component which is evidently located on only the left side. It should be noted that, in this removing operation, although the peak origin is the same, the peak height is multiplied by a certain constant, since there is a difference between vector F expressing the Q2-based filter and vector F expressing the Q3-based filter. Accordingly, in the actual removing operation, it is preferable to determine the most suitable constant by the least square method focused on only the peak portion, and perform the removing process after multiplying each intensity value by that constant. Needless to say, instead of the simple least square method, a commonly known peak-height deduction method which can deal with baseline fluctuations may be used; for example, the least square method may be applied on a waveform obtained by calculating the second derivative of F(t), or the peak height may be deduced using a matched filter with the kernel created by normalizing the extracted peak.

By repeating the previously described process until a residual signal waveform which has no noticeable peak as in the waveform denoted by Q4 in FIG. 6 is obtained, the target component and the impurities can be completely separated even when there is a plurality of impurities. In the case where a measurement signal obtained for a sample containing m kinds of substances is processed by the multistage spectrum residue method, the impurity separation process only needs to be repeated m+1 times to separate the m kinds of substances, exclusive of the occurrence of false impurity peaks due to the pH fluctuation, low-linearity of the detector or other factors.

[Configuration and Operation of Embodiment for Carrying Out Impurity Determination Process According to Previously Described Principle]

Figure 1:
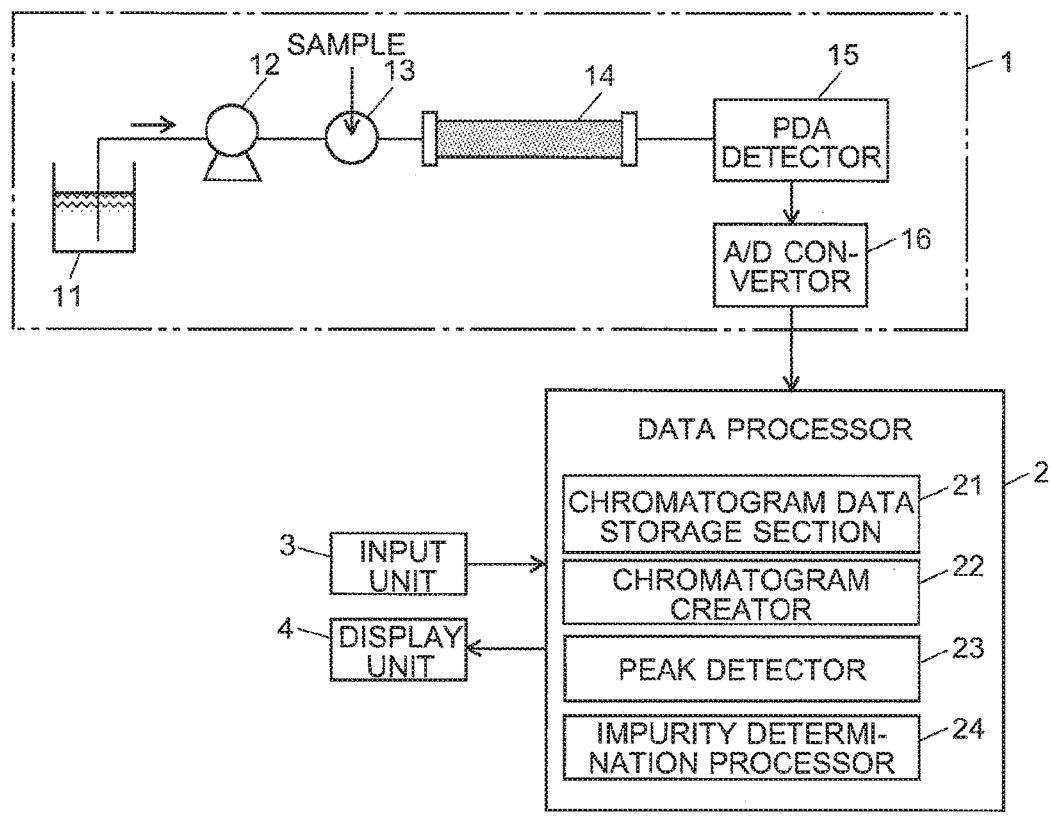
FIG. 1 is a schematic configuration diagram of one embodiment of the liquid chromatogram provided with a chromatogram data processing system according to the present invention.
Figure 2:
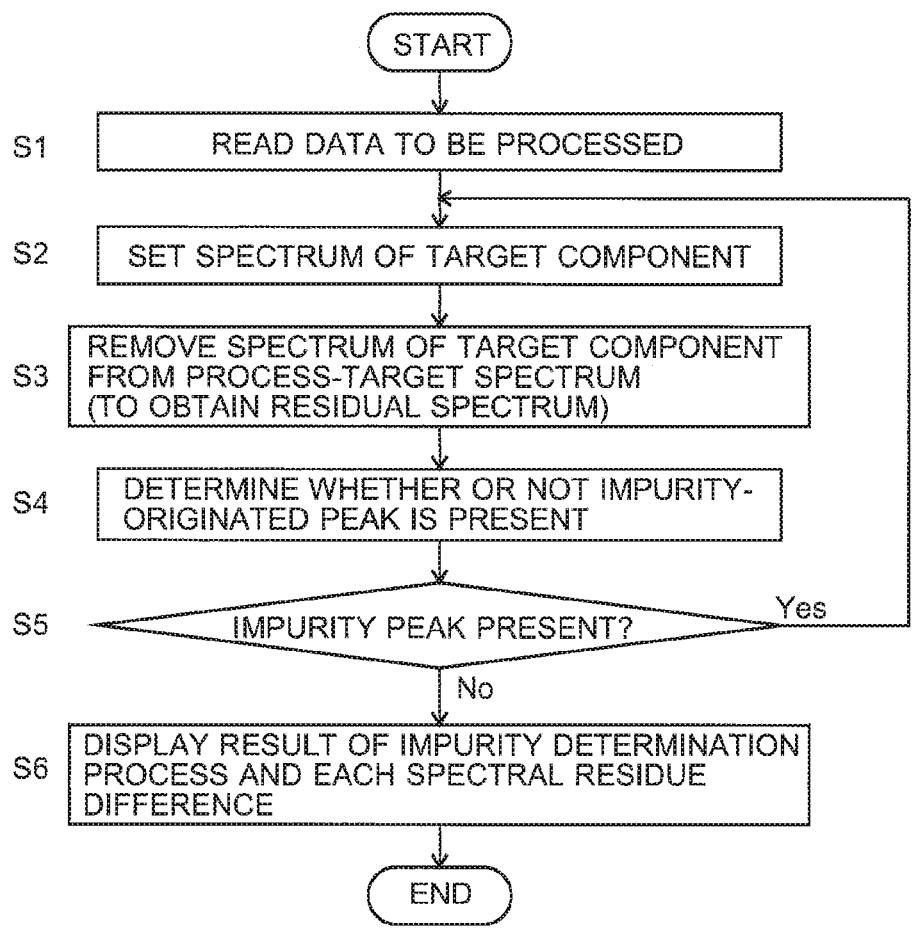
FIG. 2 is a flowchart showing the operation process for the impurity determination in the liquid chromatograph of the present embodiment.

Next, one embodiment of the liquid chromatograph provided with a chromatogram data processing system according to the present invention is described with reference to FIGS. 1 and 2. FIG. 1 is a schematic configuration diagram of the liquid chromatograph in the present embodiment.

In an LC unit 1 for collecting three-dimensional chromatogram data, a liquid-sending pump 12 suctions a mobile phase from a mobile-phase container 11 and sends it to an injector 13 at a constant flow rate. The injector 13 injects a sample liquid into the mobile phase at a predetermined timing. The sample liquid is transferred by the mobile phase to a column 14. While the sample liquid is passing through e column 14, the components in the sample liquid are temporally separated and eluted from the column 14. A PDA detector 15 is provided at the exit end of the column 14. In the PDA detector 15, light is cast from a light source (not shown) into the eluate. The light which has passed through the eluate is dispersed into component wavelengths, and the intensities of those wavelengths of light are almost simultaneously detected with a linear sensor. The detection signals repeatedly produced by the PDA detector 15 are converted into digital data by an analogue-to-digital (A/D) converter 16 and sent to a data processing unit 2 as three-dimensional chromatogram data.

The data processing unit 2 includes: a chromatogram data storage section 21 for storing three-dimensional chromatogram data; a chromatogram creator 22 for creating, from three-dimensional chromatogram data, a wavelength chromatogram which shows the temporal change in the absorbance at a specific wavelength; a peak detector 23 for detecting a peak in the wavelength chromatogram; and an impurity determination processor 24 for determining whether or not an impurity is present in a target peak specified by an analysis operator among the detected peaks. This impurity determination processor 24 is the functional block which performs the previously described characteristic process. Additionally, an input unit 3 and display unit 4 are connected to the data processing unit 2. The input unit 3 is operated by the analysis operator to enter and set items of necessary information for the data processing, such as the absorption wavelength of the target component. The display unit 4 is used for displaying various items of information, such as a chromatogram, absorption spectrum and the result of impurity determination.

A portion or the entirety of the functions of the data processor 2 and control unit (no shown) can be realized by running a dedicated controlling and processing software program installed on a personal computer or workstation. In this case, the input unit 3 includes the keyboard, pointing device (e.g. mouse) and other devices which are standard equipment of personal computers or workstations, while the display unit 4 is a commonly used liquid crystal display or similar device.

Next, the characteristic data processing operation in the liquid chromatogram of the present embodiment is described with reference to the flowchart shown in FIG. 2.

A chromatographic analysis for a target sample is performed in the LC unit 1. Three-dimensional chromatogram data (see FIG. 8A) showing the temporal change in the absorption spectrum within a predetermined wavelength range are sent from the PDA detector 15 to the data processing unit 2 and stored in the chromatogram data storage section 21. In the chromatogram data creator 22, a wavelength chromatogram at the specific wavelength or within the specific wavelength range is created based on the stored three-dimensional chromatogram data. The peak detector 23 performs a process for detecting a peak on the chromatogram. Using the input unit 3, the analysis operator designates one of the detected peaks and issues a command for executing the impurity determination process, whereupon a process which will be hereinafter described is performed:

Initially, for each point in time of the measurement within the range between the beginning point ts and the ending point te of the designated peak, the impurity determination processor 24 reads the chromatogram data (spectrum data) from the chromatogram data storage section 21 (Step S1), whereby vector I(t) which expresses the process-target spectrum is prepared (where t is within a range from ts to te).

Next, the impurity determination processor 24 sets the spectrum of the target component for calculating vector A (Step S2). As stated earlier, there are several methods for setting the spectrum of the target component. If the spectrum of the target component is already stored in a database or other data sources, that spectrum can be simply retrieved. In the present example, to deal with the situation where the spectrum of the target component is unknown and the automatic, repetitive setting of the spectrum is necessary, the technique of selecting the spectrum having the largest norm is used, since this technique requires no manual operation or judgment by the analysis operator and is capable of high-speed processing. According to this technique, the absorption spectrum obtained at the point in time of the measurement at which the largest index value of the amount of impurity u=I(t)·F has been obtained as a result of the previously performed process is directly set as the spectrum of the target component for the next process. In this manner, vector A which expresses the spectrum of the target component is also prepared.

In the first processing, i.e. when the process of Step S2 is performed for the first time, the secondary norm of vector I(t) prepared in Step S1 is calculated, and the spectrum of the target component at the point in time of the measurement at which the secondary norm is maximized is selected. Naturally, it is possible to allow the analysis operator to manually specify the spectrum of the target component. Furthermore, as described earlier, it is also possible to search for spectra which do not contain impurities, and to set the spectrum of the target component having the largest index value of the amount of impurity or the largest value of the secondary norm among the spectra which do not contain impurities.

After the process-target spectrum (vector I(t)) and the spectrum of the target component (vector A) have been determined, the filter for impurity extraction is determined in the previously described manner, and the inner product I(t)·F is calculated to remove the spectrum of the target component from the process-target spectrum and thereby determine the residual spectrum which reflects the amount of impurity (Step S3). In the present example, with the importance attached to the speed of computation, the method in which I(t)−αA at each point f the measurement is directly used as vector F(t) is adopted. In this case, the computing formulae can be transformed into simple forms; the calculation of the inner product of the vectors I(t)·F, i.e. the index value u of the amount of impurity, can be substituted by the simple calculation of the secondary norm of I(t)−αA. Naturally, various modified methods mentioned earlier may also be used, such as the average value or moving average of vector F(t), instead of determining vector F(t) at each point in time of the measurement.

Whether or not a peak originating from an impurity is present is judged by determining whether or not a peak is present in the difference between the residual spectrum determined in the previously described manner and the residual spectrum obtained in the preceding process cycle, i.e. in either the secondary norm of the spectrum residue difference or the square root of the index value of the amount of impurity ($\sqrt{(I(t) \cdot F)}$) obtained by the calculation in each cycle (Step S4). For white noise, the square root of the amount of impurity or the secondary norm of the spectrum residue difference shows a constant distribution. Therefore, the presence or absence of a peak can be confirmed by examining whether or not there is any value deviating from a certain range based on the average and standard deviation of those values. Needless to say, other methods which e ploy commonly known algorithms for detecting a chromatogram peak may also be used to confirm the presence or absence of the peak. If it is determined that an impurity peak is present, the process returns from Step S5 to Step S2 to repeat the setting of the spectrum of the target component and the removal of the spectrum of the target component. That is to say, the previously mentioned multistage spectrum residue method is carried out.

On the other hand, in Step S5, if it is determined that no impurity peak is present, the ultimate result of the impurity determination process is shown on the display unit 4 based on the already obtained determination results, and if the presence of an impurity has been confirmed, the residue difference of each spectrum is also shown on the display unit 4 (Step S6). Therefore, the analysis operator cannot only determine whether or not an impurity is superposed on the target peak but also comprehend the amount of impurity.

It should be noted that the previous embodiment is a mere example of the present invention, and any change, addition or modification appropriately made within the spirit of the present invention will evidently fall within the scope of claims of the present application.

For example, the detector used in the chromatograph for obtaining three-dimensional chromatogram data to be processed by the chromatogram data processing system of the present invention does not need to be a PDA detector or similar multichannel detector; it may alternatively be an ultraviolet visible spectrophotometer, infrared spectrophotometer, near-infrared spectrophotometer, fluorescence spectrophotometer or similar device capable of high-speed wavelength scanning. A liquid chromatograph mass spectrometer using a mass spectrometer as the detector is also available.

The chromatograph may be a gas chromatograph instead of the liquid chromatograph. As already noted, the present invention can also be evidently applied in a system which processes the data obtained by detecting the components in a sample introduced by the FIA method without being separated into components, using a PDA detector, mass spectrometer or other detectors, instead of the data obtained by detecting the sample components separated by the column of the chromatograph.

REFERENCE SIGNS LIST

1 . . . LC Unit
11 . . . Mobile-Phase Container
12 . . . Liquid-Sending Pump
13 . . . Injector
14 . . . Column
15 . . . PDA Detector
16 . . . Analogue-to-Digital (A/D) Converter
2 . . . Data Processor
21 . . . Chromatogram Data Storage Section
22 . . . Chromatogram Creator
23 . . . Peak Detector
24 . . . Impurity Determination Processor
3 . . . Input Unit
4 . . . Display Unit

The invention claimed is:

1. A chromatograph system comprising:
a chromatograph for collecting three-dimensional chromatogram data having time, signal intensity and another third dimension collected for a sample to be analyzed, the chromatograph comprising a converter for converting detected signals to digital data;
a chromatogram data processing system for processing the three-dimensional chromatogram data based on the digital data received from the converter, the system comprising a processor configured to:
calculate at least one auxiliary vector orthogonal to a principal vector, the principal vector being a multi-dimensional vector expressing a spectrum which shows or can be regarded as a relationship between the third dimension and the signal intensity for a target component to be observed,
designate the at least one auxiliary vector as a filter for impurity extraction;
calculate an inner product of a process-target multidimensional vector and the at least one auxiliary vector designated as the filter, the process-target multidimensional vector expressing a process-target spectrum obtained or derived from the three-dimensional chromatogram data obtained for the sample to be analyzed; and
determine a presence or absence of an impurity other than the target component in the process-target spectrum based on the inner product of the process-target multidimensional vector and the at least one auxiliary vector designated; and
a display connected to the chromatogram data processing system for displaying the process-target spectrum and the impurity determination.

2. The chromatograph according to claim 1, wherein:
for each of the process-target spectra obtained at the respective points in time of the measurement with the passage of time, the processor calculates the inner product of the process-target multidimensional vector expressing the process target spectrum and the at least one auxiliary vector designated as the filter, observes a change in a value of the inner product along a time series, and determines the presence or absence of the impurity other than the target component.

3. The chromatograph system according to claim 2, wherein:
the processor determines a direction of the at least one auxiliary vector expressing the filter so that a cosine similarity index between the process-target multidimensional vector expressing the process-target spectrum and the at least one auxiliary vector expressing the filter is maximized.

4. The chromatograph according to claim 3, wherein:
the processor calculates the at least one auxiliary vector comprising a plurality of auxiliary vectors, which are the filters for impurity extraction created at respective points in time of a measurement, and determines an average vector of the plurality of auxiliary vectors, and the processor uses the average vector in calculating the inner product for each process-target multidimensional vector which expresses the process-target spectrum obtained at each point in time of the measurement.

5. The chromatograph system according to claim 3, wherein:
the processor calculates the at least one auxiliary vector comprising a plurality of auxiliary vectors, which are the filter for impurity extraction created at respective points in time of a measurement, and computes a cluster mean for the plurality of auxiliary vectors, and the processor uses a vector of the cluster mean in calculating the inner product for each process-target multidimensional vector which expresses the process-target spectrum at each point in time of the measurement.

6. The chromatograph a system according to claim 3, wherein:
the processor calculates the at least one auxiliary vector comprising a plurality of auxiliary vectors, which are the filter for impurity extraction created at respective points in time of a measurement, and selects a vector having a largest norm from among the plurality of auxiliary vectors, and the processor uses the selected vector in calculating the inner product for each process-target multidimensional vector which expresses the process-target spectrum at each point in time of the measurement.

7. The chromatograph system according to claim 2, wherein:
the processor designates, as the filter for impurity extraction, a vector obtained by multiplying the principal vector expressing the spectrum of the target component by a predetermined constant and subtracting the multiplied vector from the process-target multidimensional vector expressing the process-target spectrum.

8. The chromatograph system according to claim 7, wherein:
the processor calculates a secondary norm of the vector created as the filter, by multiplying the principal vector by a predetermined constant and subtracting the multiplied vector from the process-target multidimensional vector, for impurity extraction by the processor and uses the secondary norm in place of the inner product to determine the presence or absence of an impurity in the process-target spectrum.

9. The chromatograph system according to claim 2, wherein:
the processor designates, as the spectrum of the target component, a spectrum based on data obtained within a specific period of time among the three-dimensional chromatogram data obtained for the sample to be analyzed, multiplies a vector expressing the spectrum of the target component by a predetermined constant, and designates, as the filter for impurity extraction, a vector obtained by subtracting the multiplied vector from the vector expressing the process-target spectrum, and the processor designates, as a residual spectrum, a spectrum expressed by the vector created as the filter, by multiplying the principal vector by a predetermined constant and subtracting the multiplied vector from the process-target multidimensional vector, for impurity extraction by the processor for each of the spectra obtained within a predetermined range of time including the specific period of time, and determines whether or not an impurity is present within the specific period of time by determining whether or not a peak appears before and after the specific period of time on a chromatogram created for the predetermined period of time based on the residual spectrum.

10. The chromatograph system according to claim 1, wherein:
if it is determined by the processor that an impurity is present, a spectrum expressed by the vector created as the filter, by multiplying the principal vector by a predetermined constant and subtracting the multiplied vector from the process-target multidimensional vector, for impurity extraction by the processor is designated as a residual spectrum, and process operations performed by the processor are repeated using the residual spectrum as the process-target spectrum.

11. The chromatograph system according to claim 1, wherein:
the processor selects, as the spectrum of the target component, a spectrum based on data obtained within a period of time which is estimated to include the target component free of impurities among the three-dimensional chromatogram data obtained for the sample to be analyzed, and creates a vector expressing this spectrum as the principal vector.

12. The chromatograph system according to claim 1, wherein:
the processor designates, as the principal vector, a spectrum having a largest norm when expressed in a form of a vector among the spectra based on the three-dimensional chromatogram data obtained for the sample to be analyzed.

* * * * *